(12) United States Patent
Amir et al.

(10) Patent No.: US 9,569,585 B2
(45) Date of Patent: *Feb. 14, 2017

(54) COMBINING RNAI IMAGING DATA WITH GENOMIC DATA FOR GENE INTERACTION NETWORK CONSTRUCTION

(71) Applicant: International Business Machines Corporation, Armonk, NY (US)

(72) Inventors: Arnon Amir, Saratoga, CA (US); Tanveer Fathima Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 515 days.

This patent is subject to a terminal disclaimer.

(21) Appl. No.: 14/016,619

(22) Filed: Sep. 3, 2013

(65) Prior Publication Data

US 2014/0278131 A1  Sep. 18, 2014

Related U.S. Application Data

(63) Continuation of application No. 13/835,384, filed on Mar. 15, 2013.

(51) Int. Cl.
G06F 19/00 (2011.01)
G06F 19/10 (2011.01)
G06F 19/18 (2011.01)
G06F 19/12 (2011.01)

(52) U.S. Cl.
CPC ............... *G06F 19/18* (2013.01); *G06F 19/12* (2013.01)

(58) Field of Classification Search
None
See application file for complete search history.

(56) References Cited

U.S. PATENT DOCUMENTS

| 6,203,987 | B1 | 3/2001 | Friend et al. |
| 7,181,365 | B2 | 2/2007 | Inone et al. |
| 7,496,550 | B2 | 2/2009 | Rice et al. |
| 7,542,854 | B2 | 6/2009 | Kelkar et al. |
| 2006/0263798 | A1 | 11/2006 | Huynh et al. |
| 2008/0125583 | A1 | 5/2008 | Rigoutsos et al. |
| 2010/0186119 | A1 | 7/2010 | Finer et al. |

FOREIGN PATENT DOCUMENTS

WO  03/068928  8/2003

OTHER PUBLICATIONS

Conrad et al. (Genome Research (2004) vol. 12, pp. 1130-1136).*
Markowetz and Spang (BMC Bioinformatics (2007) vol. 8 (Suppl. 6):S5 (e 1-17).*
Rodriguez et al. (Biometrika (2009) vol. 96:149-162).*
Held et al. (Nature Methods (2010) vol. 7, No. 9, pp. 747-756).*
Wang et al. ("Active Microscopic Cellular Image Annotation by Superposable Graph Transduction with Imbalanced Labels," Proc. IEEE CS Conf. Computer Vision and Pattern Recognition, 2008).*
Segal et al. (Nature Biotechnology (2007) vol. 25:675-680).*
Sonnichsen et al. (Nature 92005) vol. 434:462-469).*
Gunsalus et al. (Nature (2005) vol. 436:861-865).*
Takahashi et al., Quantitative and Temporal Analysis of Gene Silencing in Tumor Cells Induced by Small Interfering RNA or Short Hairpin RNA Expressed From Plasmid Vectors, Journal of Pharmaceutical Sciences, vol. 98, No. 1, pp. 74-80, Jan. 2009.
Rahmanto et al., Chapter 4: Identification of Distinct Changes in Gene Expression After Modulation of Melanoma Tumour Antigen p97 (Melanotransferrin) In Multiple Models In Vitro and In Vivo, Carcogenesis 28(10): 2172-83, IF 2006:5.3., 2007.

* cited by examiner

*Primary Examiner* — Lori A Clow
(74) *Attorney, Agent, or Firm* — Lieberman & Brandsdorfer, LLC

(57) ABSTRACT

Embodiments of the invention relate to a method for constructing a gene interaction network by combining two sources of genomic information, namely RNAi imaging data and gene expression data. Tools are provided to gather data, including gene expression data and gene image data, and to compute measurements and relationships, respectively. A graph is constructed with nodes representing genes and edges drawn between the nodes to form gene clusters. The graph is refined such that the shape captures a structural pattern of the cluster.

11 Claims, 5 Drawing Sheets

COMBINING RNAI IMAGING DATA WITH GENOMIC DATA FOR GENE INTERACTION NETWORK CONSTRUCTION

CROSS REFERENCE TO RELATED APPLICATION(S)

This application is a continuation patent application claiming the benefit of the filing date of U.S. patent application Ser. No. 13/835,384 filed on Mar. 15, 2013 and titled "Combining RNAi Imaging Data With Genomic Data For Gene Interaction Network Construction," now pending, which is hereby incorporated by reference.

BACKGROUND

This invention relates to gene interaction network construction. More specifically, the invention relates to combining information from two information modalities for gene interaction network construction, the former being clustering of gene expression data, and the latter being derived from morphological similarity of RNA Interference (RNAi) imaging data from the same genes.

Research in the area of biotechnology is constantly growing and evolving. Construction of a gene interaction network is sought after to provide knowledge and understanding of biological processes and diseases, and in the future may help with the identification of therapeutic compounds. Building gene interaction networks and predicting functions of genes poses a significant challenge to scientists. Model organisms are known to contain a large number of genes whose functions are unknown. Pathways, such as those for apoptosis and mitochondrial biogenesis, have only been partially identified. The rate of gene function determination significantly lags behind gene sequencing, thereby causing a backlog of genetic sequences in search of a function.

A number of approaches have been used to reveal genetic pathways, ranging from traditional low-throughput genetic screens based on phenotypes to microarray experiments that reveal gene expression similarity under various experimental conditions. In particular, visual assays using microscopy represents a medium for phenotypically assessing gene function that is complementary to microarrays. With the increasing use of RNAi through modern three dimensional restorations or confocal microscopy and high throughput imaging platforms, large amounts of image based data has become available. Microscopic imaging is a powerful tool that allows functions and aspects of cells to be studied via morphological changes, such as changes in size and shape of cells, number of subcellular organelles and structures, or the redistribution of specific proteins within the cell.

BRIEF SUMMARY

This invention comprises a method for construction of a gene interaction network.

In one aspect of the invention, a gene interaction network is constructed using gene expression analysis. Gene expression data is obtained for a first set of genes, and a recorded multi-dimensional image stack depicting groups of cells or intra-cellular structures associated with a second set of genes is obtained. A gene interaction measure between a pair of genes is computed for each pair of genes in the first set. The gene interaction measure is based upon the gene expression data. Similarly, a gene relationship measure based upon the cellular images is computed for each pair of genes in the second set. The gene relationship measure uses a morphological similarity measure between corresponding groups of cells. An initial graph is constructed. Each node in the graph is associated with at least one of the genes that belong to one of the first and second sets. Edges are drawn in the graph. Each drawn edge is based on either membership of gene clusters or morphological distance for the corresponding gene knockdown image stacks. Connectivity of a final graph is expanded using network propagation. A produced network is verified using sampling of inferred connections through designed biological experiments that elicit relationships between corresponding genes.

Other features and advantages of this invention will become apparent from the following detailed description of the presently preferred embodiment of the invention, taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments of the invention, and not of all embodiments of the invention unless otherwise explicitly indicated. Implications to the contrary are otherwise not to be made.

DETAILED DESCRIPTION

Figure 1:
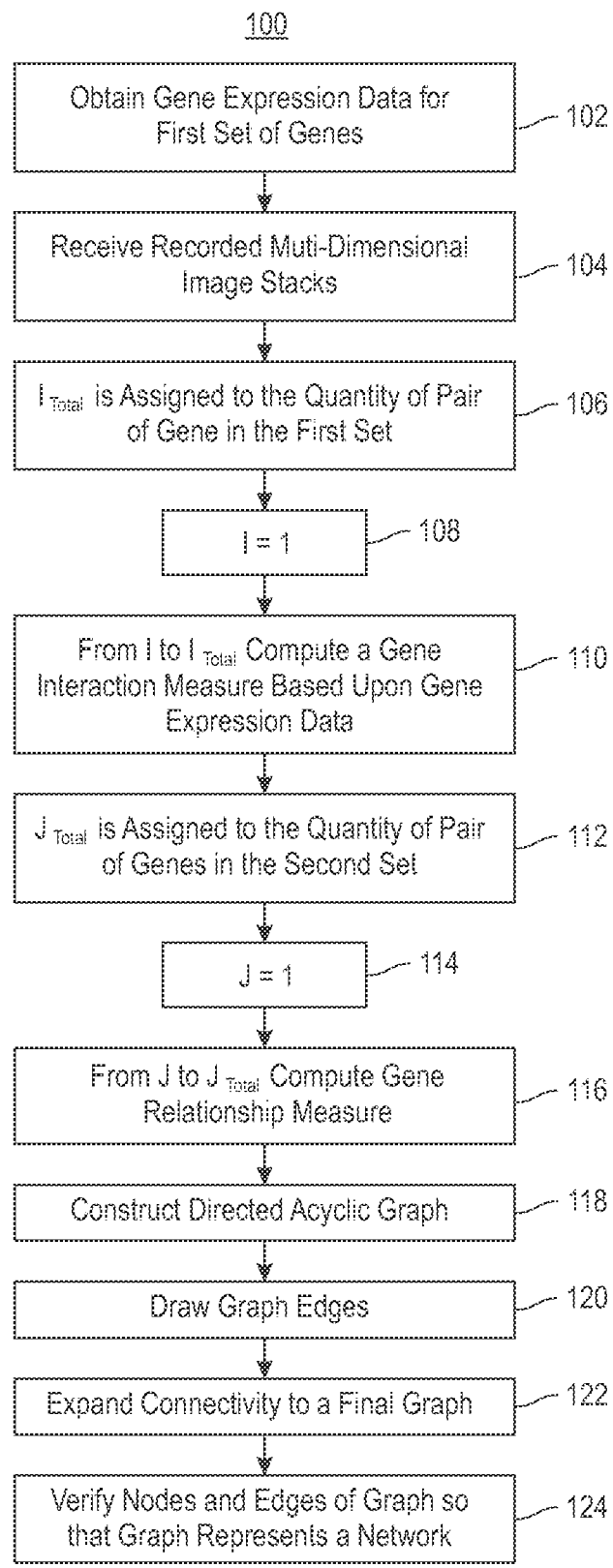
FIG. 1 is a flow chart illustrating a process for constructing a gene interaction network.

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

The functional unit described in this specification have been labeled as having managers and director(s). A functional unit may be implemented in programmable hardware devices such as field programmable gate arrays, programmable array logic, programmable logic devices, or the like. The functional unit may also be implemented in software for processing by various types of processors. An identified functional unit of executable code may, for instance, comprise one or more physical or logical blocks of computer instructions which may, for instance, be organized as an object, procedure, function, or other construct. Nevertheless, the executable of an identified functional unit need not be physically located together, but may comprise disparate instructions stored in different locations which, when joined logically together, comprise the functional unit and achieve the stated purpose of the functional unit.

Indeed, a functional unit of executable code could be a single instruction, or many instructions, and may even be distributed over several different code segments, among different applications, and across several memory devices. Similarly, operational data may be identified and illustrated herein within the functional unit, and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of managers and directors, including but not limited to an image manager, a graph manager, and a flow, to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

A cluster is known as a grouping of items that are drawn together by a mutual characteristic. The process of identifying, defining, and describing a cluster is not standardized. In the field of biotechnology it is known to subject genes to analysis under various conditions. This analysis is known as a visual assay. More specifically and as disclosed herein, visual data from the visual assay is employed to guide construction of a gene interaction network. Three dimensional morphological and shape descriptors are extracted from images of cells. Characteristics of the changes in the cells are computed. These characteristics include, but are not limited to, cell count, volume, higher moments, surface area, three dimensional textures, and edges. Based upon the computations, features of the cells and their morphological similarity among images of cells are exploited. In one embodiment, the similarity is employed to construct a directed acyclic graph for related images stacks thereby connecting the respective genes in a mathematical and graphical relationship. From this graph, gene clusters and associated cluster membership is formed and verified. Accordingly, structural clusters are formed with the membership pertaining to relationships among corresponding genes.

Gene expression data associated with the visual data provides a positive indication of the effect of a gene, i.e. the effect on the cells when a gene is expressed. A complementary piece of information is available through gene knockdown experiments in which a gene is removed from the cell (gene silenced) and the effect on the cells is studied. The process is called RNAi (RNA interference) where for each three dimensional segmented region of the cells, changes in the cell or nucleus appearance induced by a particular RNAi is measured. RNAi is the introduction of double-stranded ribonucleic acid (RNA) into a cell to inhibit the expression of a gene. The gene knockdown experiments are typically performed through visual assays. Imaging devices, including photon microscopes and high resolution electron tomography, are used to study the changes in cellular morphology. Accordingly, the gene knockdown information can be used as a complementary cue to infer a network.

There are two fundamental measures that are employed in constructing a gene interaction network, including a gene interaction measure and a gene relationship measure. FIG. 1 is a flow chart (100) illustrating a process for constructing a gene interaction network. Gene expression data is obtained for a first set of genes (102). In one embodiment, the gene expression data is acquired in response to experiments on a set of genes, with the experiments done under multiple environmental conditions. Recorded multi-dimensional image stacks are received (104). In one embodiment, the image stacks represent groups of cells or intra-cellular structures associated with a second set of genes. The groups received at step (104) are created by knocking down one or more genes from a second set of genes. In one embodiment, the first set of genes and the second set of genes include common genes. The variable $i_{Total}$ is assigned to represent the quantity of pairs of genes in the first set (106), and a counting variable i is set to the integer one (108). For each pair of genes in the first set from i to $i_{Total}$, a gene interaction measure is computed based upon the gene expression data (110). Details associated with computing the gene interaction measure are illustrated and described in FIG. 2. The variable $j_{Total}$ is assigned to represent the quantity of pairs of genes in the second set (112), and a counting variable j is set to the integer one (114). For each pair of genes in the second set from j to $j_{Total}$, a gene relationship measure is computed (116). In one embodiment, the computation at step (116) is based upon cellular images using a morphological similarity measure between corresponding groups of cells. Accordingly, the first part of the construction of the network requires two sets of computations, each of the computations associated with first and second sets of genes, respectively.

Following the computations at steps (110) and (116), a directed acyclic graph is constructed (118). Each node in the constructed graph is associated with one of the genes belonging to one of the first and second sets. More specifically, each node in the graph represents either gene expression or cellular imaging studies. A part of the graph construction includes drawing edges between a set of nodes. Edges are drawn based on either membership of gene cluster or morphological distance for the corresponding gene knockdown image stacks (120). Using network propagation, the connectivity of the graph is expanded to a final graph (122). Once the graph is complete, verification of the nodes and the edges is conducted such that the graph represents a network (124). In one embodiment, the verification takes place by sampling inferred connections through one or more designed biological experiments, thereby eliciting relationships between corresponding genes. Accordingly, the nodes in the constructed graph represent genes and the edges represent connections and relationships between the genes.

Figure 2:
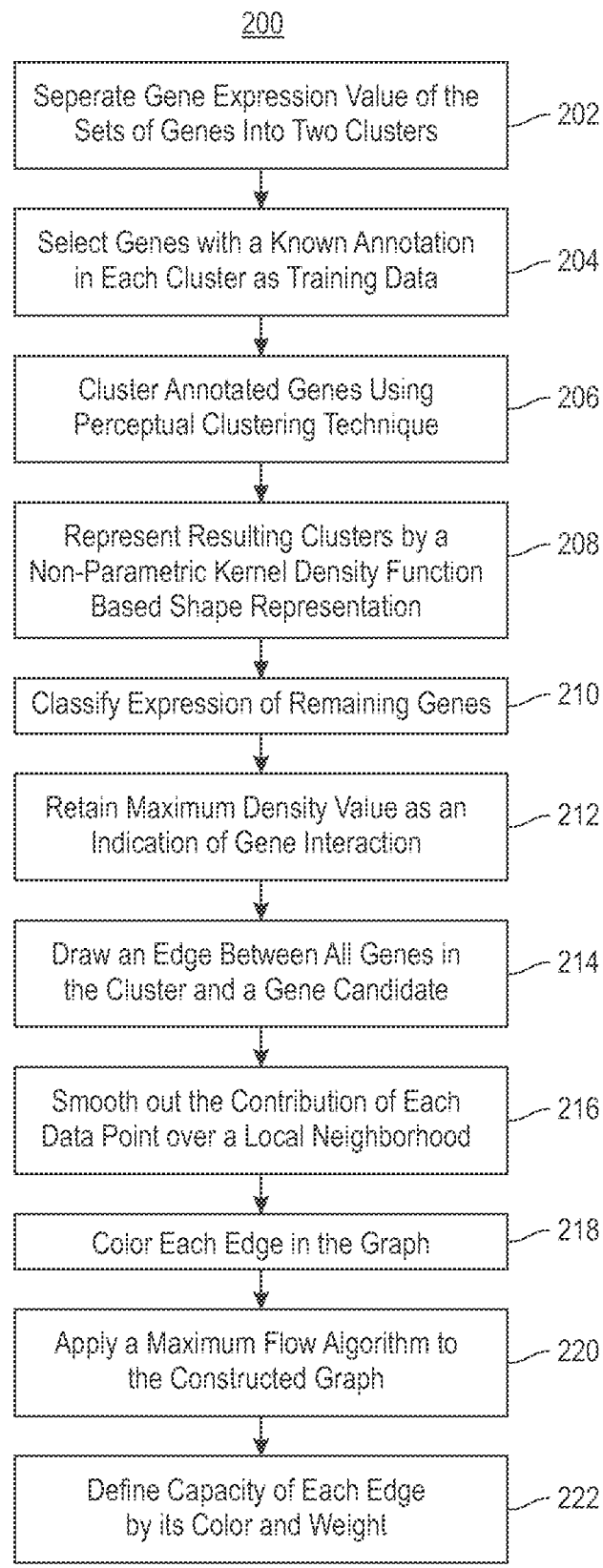
FIG. 2 is a flow chart illustrating details for computing the gene interaction measure between a pair of genes.

As shown in FIG. 1, a gene interaction measure is computed for a first set of genes based upon the gene expression data. FIG. 2 is a flow chart (200) illustrating the details for computing the gene interaction measure between a pair of genes. Gene expression values of the set of genes and associated with an experimental condition are separated into two clusters (202). The separation is based on differential expression with respect to a control in a corresponding environmental condition of one of the associated experiments. Genes with a known annotation in each cluster are selected as training data (204), and the annotated genes are clustered using a perceptual clustering technique (206). The resulting clusters are represented by a non-parametric kernel density function based shape representation (208). An expression of the remaining genes is classified (210). The classification includes evaluating kernel density functions of stored clusters and using a maximum density value to classify the gene expression. The maximum density value is retained as an indication of gene interaction (212). An edge is drawn between all genes in the corresponding cluster and a candidate gene (214), and the contribution of each data point over a local neighborhood of that data point is smoothed out (216). Accordingly, by drawing edges between the represented genes, a pairwise gene interaction measure is formed.

A two-colored graph is created by combining the information from RNAi imaging and gene expression information. Nodes in the graph represent selected genes in the chosen interaction pathway. Each pair of nodes may be connected by two sets of edges of different color. The weight of an edge reflects a similarity score between the genes while the color represents the choice of the modality. In one embodiment, the constructed graph is referred to as a Bayesian network, and the network is partitioned into functional modules that correspond to sets of genes that are part of the same biological pathway based on morphological similarity. Whether aspects of the constructed graph are partitioned or remain intact, each edge in the graph is colored (218). The application of color is an indication of a modality of an underlying gene. A maximum flow algorithm is applied to the constructed graph (220). Genes represented in the vertices of the graph with a known function annotation are designated as source nodes, and color and weight of the respective edges are exploited as a conduit. A flow will not be diverted along a conduit of a different color. In one embodiment, capacity of each edge is defined by its color and weight (222). Accordingly, the gene expression data is portrayed in a directed acyclic graph with the vertices and edges representing characteristics of the relationship among image stacks.

Figure 3:
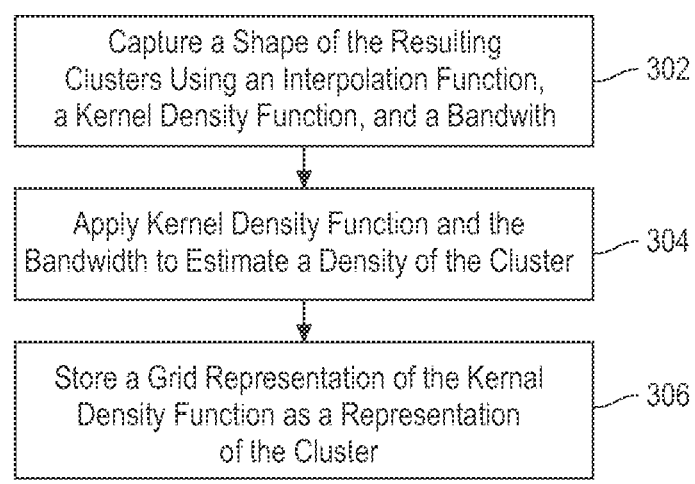
FIG. 3 is a flow chart illustrating a process for forming and describing the shape and density of the constructed gene interaction network.

Following formation of the network, the characteristics of the network are further evaluated and described. More specifically, the shape and density of the network are described. FIG. 3 is a flow chart (300) illustrating a process for forming and describing the shape and density of the network. As described above, the gene interaction measure and the gene relationship measure are computed for two sets of genes. Based upon these measurements, a directed acyclic graph is constructed and a network is formed. A shape of the resulting clusters is captured using an interpolation function, a kernel density function, and an associated bandwidth (302). The kernel density function and the bandwidth are applied to estimate a density of the cluster (304). In one embodiment, selection of the bandwidth affects the smoothness in both the shape and accuracy of shape representation. Similarly, in one embodiment, the interpolation and shape representation of the cluster is a function of the bandwidth, and the kernel density function is a continuous formulation thereby providing a dense shape description of the cluster. Following step (304), a grid representation of the kernel density function is stored as a representation of the cluster (306). Accordingly, the kernel density function is applied to the formed network to produce and describe a cluster shape, wherein the choice of the bandwidth creates a tradeoff between smoothness of the cluster shape and accuracy of the shape representation.

Figure 4:
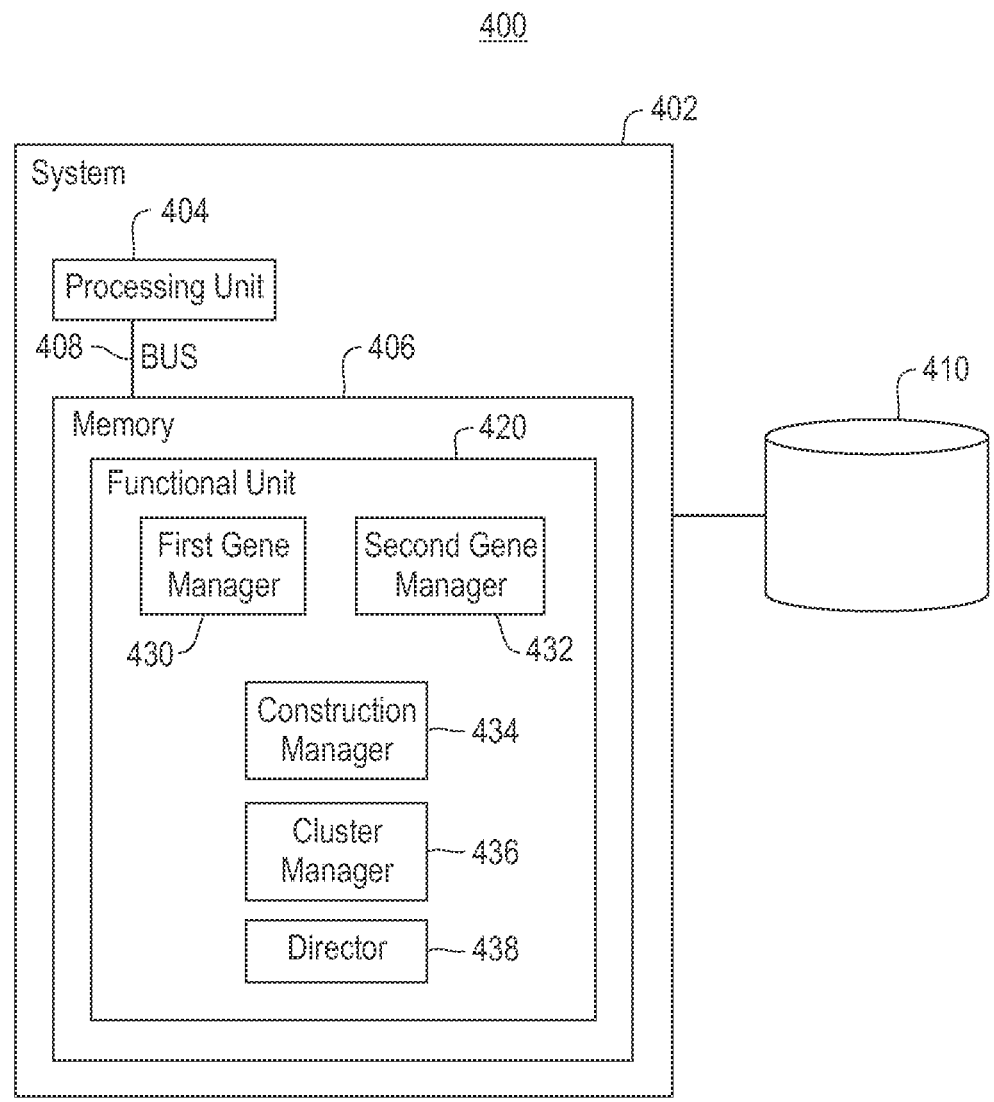
FIG. 4 is a block diagram illustrating tools embedded in a computer system to support construction of the gene interaction network.

As demonstrated in the flow charts of FIGS. 1-3, a gene interaction network is constructed using gene expression analysis by employing both a gene interaction measure and a gene relationship measure. FIG. 4 is a block diagram (400) illustrating tools embedded in a computer system to support construction of the gene interaction network described above. A computer system (402) is shown with a processing unit (404) in communication with memory (406) across a bus (408) and in communication with data storage (410). In one embodiment, the data storage (410) is remotely accessed across a network (not shown). A functional unit (420) is provided in communication with the memory (406). The functional unit (420) is provided to support construction of the gene interaction network. More specifically, the functional unit (420) includes a plurality of managers and a director to support the construction, including a first gene manager (430), a second gene manager (432), a construction manager (434), a cluster manager (436), and a director (438).

The first gene manager (430) functions to obtain gene expression data of a first set of genes and to compute a gene interaction measure between a pair of genes based upon the gene expression data. In one embodiment, the gene expression data is acquired in response to multiple environmental conditions associated with experiments. The second gene manager (432) functions to receive a recorded multi-dimensional image stack depicting a group of cells or intra-cellular structure associated with a second set of genes, and to compute a gene relationship measure based upon the cellular images using a morphological similarity measure between corresponding groups of cells. In one embodiment, each of the groups of cells is received by knocking down one or more genes from the second set of genes. Accordingly, the first and second gene managers (430) and (432), respectively, function to separately compute gene interaction measurements and gene relationship measurements.

The construction manager (434) is provided in communication with both the first gene manager (430) and the second gene manager (432). The construction manager (434) functions to construct an initial directed acyclic graph. Each node in the graph is associated with one of the genes belong to one of the first and second sets of genes. In addition, the construction manager (434) draws edges between the nodes, with the edges drawn based on either membership of gene clusters or morphological distance for the corresponding gene knockdown image stacks. Following creation of the initial graph, the construction manager (434) may expand connectivity among the nodes based upon network propagation thereby creating a final graph. The director (438) communicates with the construction manager (434) to verify a produced network associated with the graph. More specifically, the director (438) samples inferred connections through designed biological experiments, thereby eliciting the relationships between the corresponding genes. In one embodiment, the director (438) colors each edge in the graph. The application of color is an indication of a modality of an underlying gene. A maximum flow algorithm is applied to the constructed graph by the director (438). Genes represented in the vertices of the graph with a known function annotation are designated as source nodes, and color and weight of the respective edges are exploited as a conduit. A flow will not be diverted along a conduit of a different color. In one embodiment, capacity of each edge is defined by its color and weight. Accordingly, the managers and director function to both create the initial network, expand the created network, and to verify the created network.

As described above, the first gene manager (430) functions to compute the gene interaction measurement. The aspect of the computation by the first gene manager (430) includes separation of gene expression values of the set of genes and associated with an experimental condition into two clusters. The separation is based on differential expressions with respect to a control in a corresponding environmental condition of one of the associated experiments. Genes with a known annotation in each cluster are selected as training data, and the annotated genes are clustered using a perceptual clustering technique. The resulting clusters are represented by a non-parametric kernel density function based shape representation, and an expression of the remaining genes is classified. The classification includes evaluating kernel density functions of stored clusters and using a maximum density value to classify the gene expression. The maximum density value is retained as an indication of gene interaction. An edge is drawn between all genes in the corresponding cluster and a candidate gene, and the contribution of each data point over a local neighborhood of that data point is smoothed out. Accordingly, by drawing edges between the represented genes, a pairwise gene interaction measure is formed by the first gene manager (430).

As shown in FIG. 4, a cluster manager (436) is provided in communication with the first gene manager (430). The cluster manager (436) functions to estimate a density of the formed cluster. More specifically, the cluster manager (436) captures a shape of the resulting clusters using an interpolation function, a kernel density function, and an associated bandwidth. The kernel density function and the bandwidth are applied by the cluster manager (436) to estimate the density of the cluster. In one embodiment, selection of the bandwidth by the cluster manager (436) affects the smoothness in both the shape and accuracy of shape representation. Similarly, in one embodiment, the interpolation and shape representation of the cluster is a function of the bandwidth, and the kernel density function is a continuous formulation thereby providing a dense shape description of the cluster. Following creation of the cluster by the cluster manager (436), a grid representation of the kernel density function is stored as a representation of the cluster. In one embodiment, the cluster manager (436) stores the kernel density function in data storage (410). Accordingly, the kernel density function is applied by the cluster manager to the formed network to produce and describe a cluster shape, wherein the choice of the bandwidth creates a tradeoff between smoothness of the cluster shape and accuracy of the shape representation.

As identified above, first gene manager (430), second gene manager (432), construction manager (434), cluster manager (436), and director (438) function to support construction of the gene interaction network described above. The managers and the director are shown residing in memory (406) in communication with a processor (404). More specifically, the first gene manager (430), second gene manager (432), construction manager (434), cluster manager (436), and director (438) each reside in the functional unit local to memory (406). In one embodiment, the first gene manager (430), second gene manager (432), construction manager (434), cluster manager (436), and director may reside as hardware tools external to memory (406), or they may be implemented as a combination of hardware and software. Similarly, in one embodiment, the managers and the director may be combined into a single functional item that incorporates the functionality of the separate items. As shown herein, each of the managers and the director is shown local to a single processing unit (404). However, in one embodiment the managers and the director may be collectively or individually distributed across a network and function as a unit to construct a gene interaction network. Accordingly, the managers and the director may be implemented as software tools, hardware tools, or a combination of software and hardware tools, to collect and organize data content.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Matlab or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
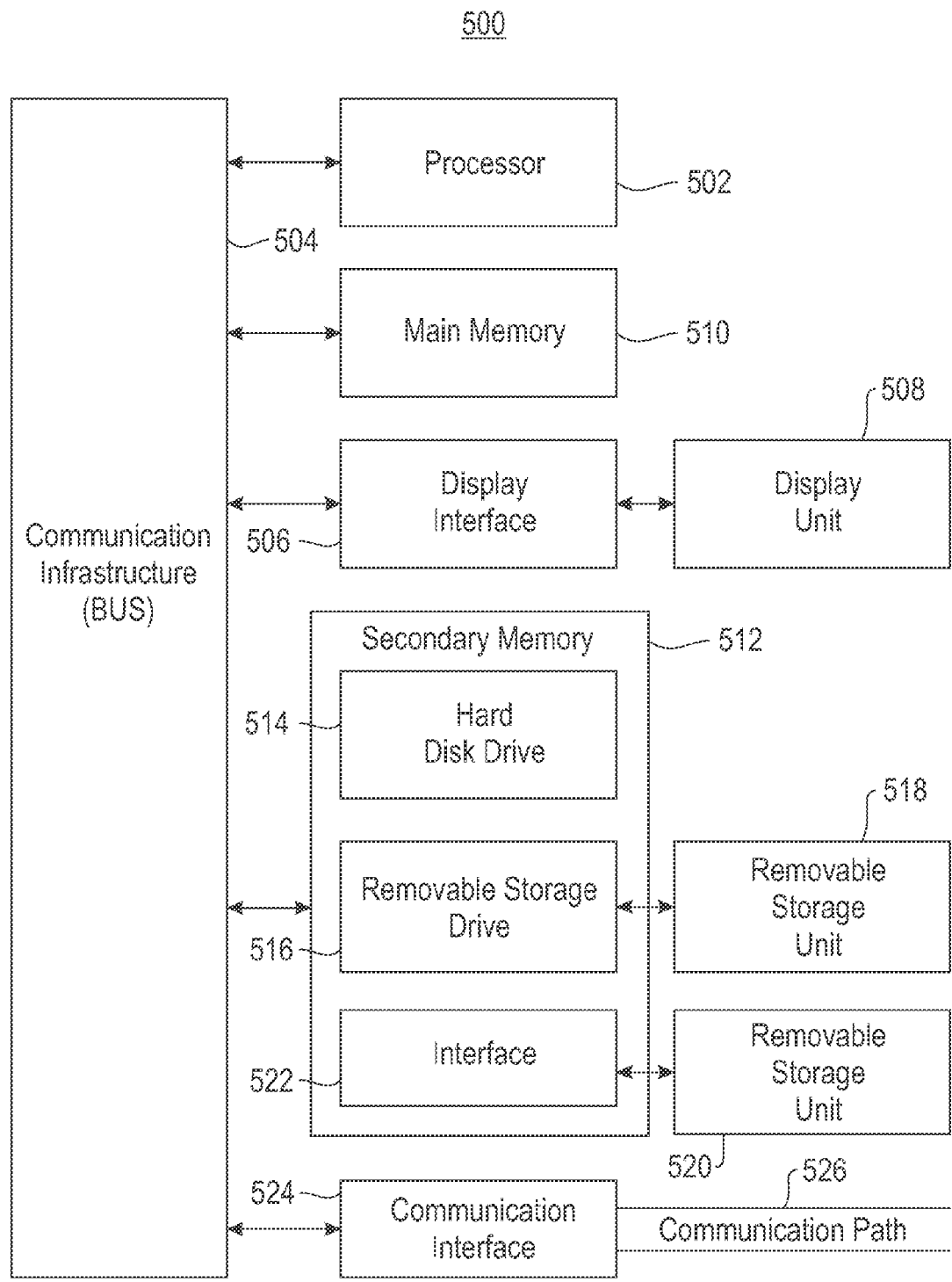
FIG. 5 is a block diagram showing system for implementing an embodiment of the present invention.

Referring now to FIG. 5 is a block diagram showing a system for implementing an embodiment of the present invention. The computer system includes one or more processors, such as a processor (502). The processor (502) is connected to a communication infrastructure (504) (e.g., a communications bus, cross-over bar, or network). The computer system can include a display interface (506) that forwards graphics, text, and other data from the communication infrastructure (504) (or from a frame buffer not shown) for display on a display unit (508). The computer system also includes a main memory (510), preferably random access memory (RAM), and may also include a secondary memory (512). The secondary memory (512) may include, for example, a hard disk drive (514) and/or a removable storage drive (516), representing, for example, a floppy disk drive, a magnetic tape drive, or an optical disk drive. The removable storage drive (516) reads from and/or writes to a removable storage unit (518) in a manner well known to those having ordinary skill in the art. Removable storage unit (518) represents, for example, a floppy disk, a compact disc, a magnetic tape, or an optical disk, etc., which is read by and written to by removable storage drive (516). As will be appreciated, the removable storage unit (518) includes a computer readable medium having stored therein computer software and/or data.

In alternative embodiments, the secondary memory (512) may include other similar means for allowing computer programs or other instructions to be loaded into the computer system. Such means may include, for example, a removable storage unit (520) and an interface (522). Examples of such means may include a program package and package interface (such as that found in video game devices), a removable memory chip (such as an EPROM, or PROM) and associated socket, and other removable storage units (520) and interfaces (522) which allow software and data to be transferred from the removable storage unit (520) to the computer system.

The computer system may also include a communications interface (524). Communications interface (524) allows software and data to be transferred between the computer system and external devices. Examples of communications interface (524) may include a modem, a network interface (such as an Ethernet card), a communications port, or a PCMCIA slot and card, etc. Software and data transferred via communications interface (524) are in the form of signals which may be, for example, electronic, electromagnetic, optical, or other signals capable of being received by communications interface (524). These signals are provided to communications interface (524) via a communications path (i.e., channel) (526). This communications path (526) carries signals and may be implemented using wire or cable, fiber optics, a phone line, a cellular phone link, a radio frequency (RF) link, and/or other communication channels.

In this document, the terms "computer program medium," "computer usable medium," and "computer readable medium" are used to generally refer to media such as main memory (510) and secondary memory (512), removable storage drive (516), and a hard disk installed in hard disk drive (514). Computer programs (also called computer control logic) are stored in main memory (510) and/or secondary memory (512). Computer programs may also be received via a communication interface (524). Such computer programs, when run, enable the computer system to perform the features of the present invention as discussed herein. In particular, the computer programs, when run, enable the processor (502) to perform the features of the computer system. Accordingly, such computer programs represent controllers of the computer system.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Alternative Embodiment

It will be appreciated that, although specific embodiments of the invention have been described herein for purposes of illustration, various modifications may be made without departing from the spirit and scope of the invention. Accordingly, the scope of protection of this invention is limited only by the following claims and their equivalents.

We claim:

1. A computer implemented method for construction of a gene interaction network, comprising:
    for each pair of genes in a first set of gene expression data, computing a first gene interaction measure between a pair of genes based upon said gene expression data, the computation comprising:
    clustering genes from the first set based on the expression data, the clustering comprising:
    separating gene expression values of the set of genes, obtained under an experimental condition, into two clusters based on differential expression with respect to a control in a corresponding environmental condition of associated experiments; and
    selecting genes with known annotation in each cluster as training data, and further clustering the annotated genes using perceptual clustering;
    capturing a shape of the resulting clusters using an interpolation function, a kernel density function, and an associated bandwidth;
    continuously formulating the kernel density function to provide a dense shape description of the clusters; and
    storing the kernel density function as a representation of the clusters;
    generating a multi-dimensional image stack via RNAi screening for each pair of genes in a second set having image data from the stack depicting groups of cells or intra-cellular structures associated with the second set of genes;
    computing a gene relationship measure using a morphological similarity measure between corresponding groups of cells, wherein the morphological similarity measure is a value computed by comparison of morphological features on paired cellular images; and
    constructing an initial graph based on the gene interaction and gene relationship measures including:
    combining the first set of gene expression data with the image data of the second set, each node in the graph associated with one of the genes belonging to one of the first and second sets and drawing edges between nodes, the edges based on membership of gene clusters or morphological distance for corresponding gene knockdown image stacks; and
    constructing a final graph by expanding connectivity among the nodes in the graph using network propagation, the expanded connectivity forming the gene interaction network.

2. The method of claim 1, wherein computing the gene interaction measure between a pair of genes further comprises:
    representing resulting clusters by a non-parametric kernel density function-based shape representation;
    classifying an expression of remaining genes, including evaluating kernel density functions of stored clusters and using a maximum density value to classify the gene expression; and
    storing the maximum density value as an indication of gene interaction; and
    drawing an edge between all genes in the corresponding cluster and a candidate gene to form a pairwise gene interaction measure.

3. The method of claim 2, further comprising applying the kernel density function and the associated bandwidth to estimate a density of the cluster, wherein selection of the bandwidth affects smoothness in shape and accuracy of shape representation.

4. The method of claim 1, wherein the interpolation and shape representation of the cluster is a function of the bandwidth.

5. The method of claim 1, further comprising coloring each edge in the graph, with the applied color indicating a modality of an underlying gene.

6. The method of claim 1, further comprising applying a maximum flow algorithm to the constructed graph in which genes with a known function annotation are designated as source nodes, and color and weight of the edge are exploited as a conduit.

7. The method of claim 6, wherein capacity of the edge is defined by color and weight.

8. A method for construction of a gene interaction network, comprising:
    for each pair of genes in a first set of gene expression data, computing a first gene interaction measure between a pair of genes based upon said gene expression data, the computation comprising:
    clustering genes from the first set based on the expression data, the clustering comprising:
    separating gene expression values of the set of genes, obtained under an experimental condition, into two clusters based on differential expression with respect to a control in a corresponding environmental condition of associated experiments; and
    selecting genes with known annotation in each cluster as training data, and further clustering the annotated genes using perceptual clustering;
    classifying expression of remaining genes, including evaluating kernel density functions of stored clusters and using a maximum density value to classify the gene expression and provide a dense shape description of the clusters;

storing the kernel density functions as a representation of the clusters;

generating a multi-dimensional image stack via RNAi screening for each pair of genes in a second set having image data from the stack depicting groups of cells or intra-cellular structures associated with the second set of genes;

computing a gene relationship measure using a morphological similarity measure between corresponding groups of cells, wherein the morphological similarity measure for each pair of genes is a value computed by comparison of morphological features on paired cellular images; and constructing an initial graph based on the gene interaction and gene relationship measures, including:

combining the first set of gene expression data with the image data of the second set, each node in the graph associated with one of the genes belonging to one of the first and second sets and drawing edges between nodes, the edges based on membership of gene clusters or morphological distance for corresponding gene knockdown image stacks; and constructing a final graph by expanding connectivity among the nodes in the graph using network propagation, the expanded connectivity forming the gene interaction network.

9. The method of claim 8, wherein computing the interaction measure between a pair of genes further comprises:

representing resulting clusters by a non-parametric kernel density function-based shape representation; and retaining a maximum density value as an indication of gene interaction, including drawing an edge between all genes in the corresponding cluster and a candidate gene to form a pairwise gene interaction measure.

10. The method of claim 9, further comprising applying an interpolation function to estimate a density of the cluster, including selecting a bandwidth to provide smoothness in shape and accuracy of shape representation.

11. The method of claim 9, further comprising storing a grid representation of the kernel density function as a representation of the cluster.

* * * * *